United States Patent
Covey et al.

(10) Patent No.: US 7,526,345 B2
(45) Date of Patent: Apr. 28, 2009

(54) ASSESSING MEDICAL ELECTRODE CONDITION

(75) Inventors: Kevin K. Covey, Marysville, WA (US);
Thomas J. McGrath, Everett, WA (US);
Joseph L. Sullivan, Kirkland, WA (US);
Larry R. Nygaard, Snohomish, WA (US); Richard C. Nova, Kirkland, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 84 days.

(21) Appl. No.: 10/865,232

(22) Filed: Jun. 10, 2004

(65) Prior Publication Data
US 2005/0277991 A1 Dec. 15, 2005

(51) Int. Cl.
*A61N 1/39* (2006.01)
(52) U.S. Cl. .............. 607/142; 607/5; 607/8; 206/210; 206/438; 324/689
(58) Field of Classification Search .......... 607/8, 607/5, 142; 206/438, 210; 324/689
See application file for complete search history.

(56) References Cited

U.S. PATENT DOCUMENTS

| 4,979,517 | A | 12/1990 | Grossman et al. |
| 5,899,925 | A * | 5/1999 | Ochs et al. ............ 607/5 |
| 5,984,102 | A | 11/1999 | Tay |
| 6,304,780 | B1 | 10/2001 | Owen et al. |
| 6,546,285 | B1 | 4/2003 | Owen et al. |
| 6,560,485 | B2 * | 5/2003 | Herleikson ............ 607/27 |
| 6,603,318 | B2 | 8/2003 | Hansen et al. |
| 2003/0055478 | A1 * | 3/2003 | Lyster et al. ............ 607/142 |
| 2003/0083729 | A1 * | 5/2003 | Solosko et al. ......... 607/142 |

* cited by examiner

*Primary Examiner*—Carl H Layno
*Assistant Examiner*—Deborah Malamud
(74) *Attorney, Agent, or Firm*—Shumaker & Sieffert, P.A.

(57) ABSTRACT

The invention presents an apparatus and techniques for determining whether a medical electrode, such as a defibrillation electrode coupled to an automated external defibrillator, is in a condition for replacement. The determination can be made as a function of one or more data. In one exemplary embodiment, the determination is a function of one or more measurements of an impedance of a hydrogel bridge in a test module. In another exemplary embodiment, the determination is a function of one or more environmental condition data from one or more environmental sensors.

23 Claims, 9 Drawing Sheets

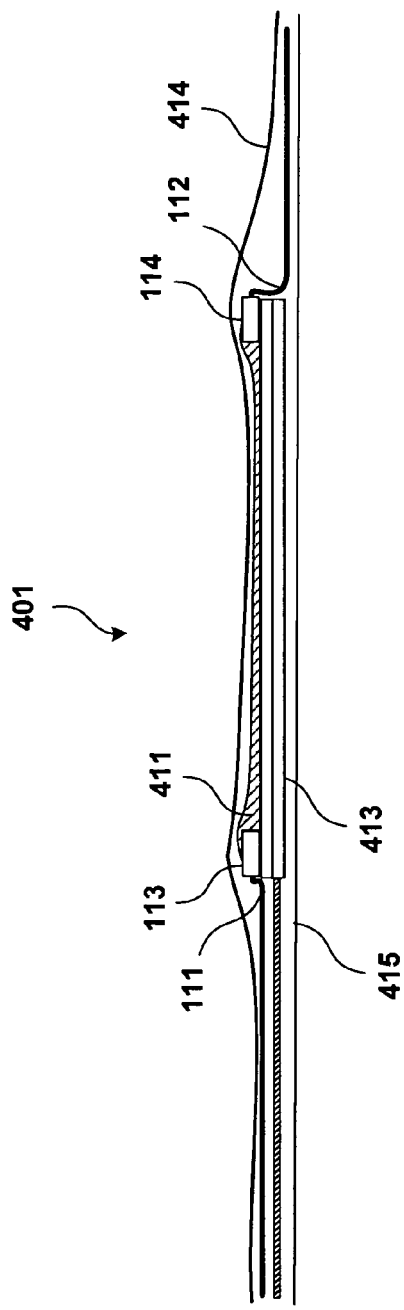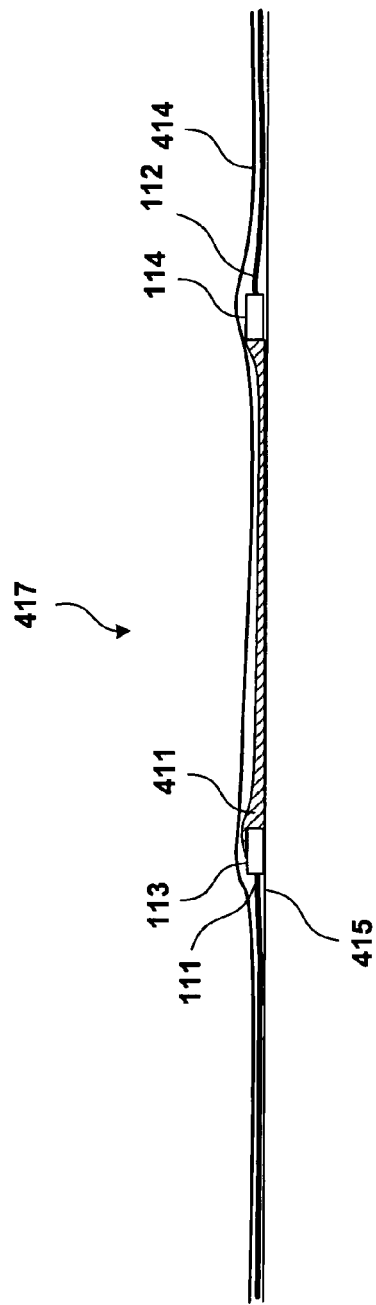

ASSESSING MEDICAL ELECTRODE CONDITION

TECHNICAL FIELD

The invention relates to medical devices for monitoring or treating medical conditions, and more particularly, to external medical devices including but not limited to external defibrillators.

BACKGROUND

Fibrillation is a life-threatening medical condition that may be treated with external defibrillation. External defibrillation includes applying defibrillation electrodes to the patient's chest and delivering an electric shock to the patient to depolarize the patient's heart and restore normal sinus rhythm. The chances that a patient's heart can be successfully defibrillated increase significantly if a defibrillation pulse is applied quickly. In many venues, such as airports, health clubs and auditoriums, automated external defibrillators (AEDs) are available to provide life-saving defibrillation therapy. Such AEDs may be used infrequently, in comparison to external defibrillators employed by rescue personnel.

An AED includes defibrillation electrodes, which an operator applies to the chest of the patient and which deliver the defibrillation therapy. The electrodes are typically disposable and are stored within hermetically sealed packages. Sealing electrodes in a package provides protection during shipping, maintains sterility, and prolongs the useful life of the electrodes.

For example, electrode pads include a hydrogel that helps adhere the electrode to the patient, enhances electrical contact between the electrode and the patient, and facilitates administration of a defibrillation shock with a reduced risk of burning the patient. The shelf life of electrode pads is in part a function of the shelf life of the hydrogel. In time, moisture evaporates out of the hydrogel and escapes from the package. As moisture escapes, the safety and effectiveness of the defibrillation electrodes may become compromised. As the hydrogel dries, the defibrillation electrode may become less adhesive, may be less able to detect electrical signals generated by the patient's heart, and may conduct defibrillation shock less efficiently. When the defibrillation electrodes are in a condition in which they are unable to perform appropriately, or are at risk of being unable to perform appropriately, then the defibrillation electrodes are in a condition for replacement.

SUMMARY

In general, the invention is directed to apparatus and corresponding techniques for determining whether one or more medical electrodes coupled to a medical device are in condition for replacement. The invention will be illustrated in the context of defibrillation electrodes that are coupled to an AED, but the invention is not limited to this application. Various embodiments of the invention may be useful with other medical devices that employ medical electrodes, such as medical monitors.

Defibrillation electrodes can be in condition for replacement even if the defibrillation electrodes are still usable. The defibrillation electrodes can be in condition for replacement when the defibrillation electrodes have exceeded a useful shelf life, for example, or when the defibrillation electrodes have been exposed to environmental conditions that put them at risk of being unable to perform appropriately. In the event the defibrillation electrodes are in condition for replacement, the AED notifies a person via an output device, such as an alarm, or via a communication to another device such as a central station.

The determination can be made as a function of one or more data. For example, the determination can be a function of one or more measurements of an impedance of a hydrogel bridge in a test module. The impedance of the hydrogel bridge in the test module is indicative of the quality of the hydrogel that is in contact with the defibrillation electrodes. Increases in the magnitude of the impedance, for example, result from drying of the hydrogel, and drying of the hydrogel affects the efficacy of the hydrogel. Accordingly, an increase in the magnitude of the impedance of the hydrogel bridge of the test module can indicate potential drying of the hydrogel on the defibrillation electrodes. An AED can be equipped with an impedance measure circuit to measurements the impedance of the hydrogel bridge in a test module.

The determination can also be a function of one or more environmental condition data sensed by one or more environmental sensors. Environmental conditions such as temperature and humidity generally affect the efficacy of the hydrogel. Low humidity, or high temperatures, or both can reduce the efficacy of the hydrogel. An AED can be equipped with one or more environmental sensors that collect environmental condition data. The invention supports embodiments in which the AED updates the usable shelf life, such as by extending or shortening the expiration date of the defibrillation electrodes, in response to the environmental condition data.

In one embodiment, the invention is directed to a method comprising measuring an impedance between a first test lead and a second test lead in electrical contact with a hydrogel bridge, and determining whether a medical electrode coupled to a medical device is in a condition for replacement as a function of the measurement. In this embodiment, the first test lead and the second test lead are electrically isolated from the medical electrode. The medical electrode can comprise a defibrillation electrode, and the medical device can comprise an AED.

In another embodiment, the invention presents a method comprising receiving at least one environmental condition datum from an environmental sensor and determining whether a medical electrode coupled to a medical device is in a condition for replacement as a function of the datum. The environmental condition datum may include a temperature datum or a humidity datum, or both, but is not limited to those environmental condition data. Furthermore, the techniques that take environmental condition data into consideration may be combined with the techniques that take impedance into consideration.

The invention also includes embodiments in which a computer-readable medium comprising instructions causes a programmable processor to carry out any of the above methods.

In a further embodiment, the invention is directed to a device that includes a first test lead, a second test lead, and a hydrogel bridge in electrical contact with the first and second test leads. The first test lead and the second test lead are electrically isolated from a medical electrode coupled to a medical device. In addition, the test module includes a hermetically sealed package containing the first and second test leads and the hydrogel bridge.

In an additional embodiment, the invention is directed to an automated external defibrillator comprising an impedance measure module configured to measure an impedance between a first test lead and a second test lead in electrical contact with a hydrogel bridge, in which the first test lead and the second test lead are electrically isolated from a defibrillation electrode coupled to the automated external defibrillator. The automated external defibrillator also includes a processor configured to determine whether the defibrillation electrode is in a condition for replacement as a function of the measurement.

In another embodiment, the invention is directed to an automated external defibrillator that includes a processor configured to receive at least one environmental condition datum from an environmental sensor and to determine the defibrillation electrode to be in a condition for replacement as a function of the datum.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 4A is a cross-sectional view illustrating an example defibrillation electrode with test leads.

FIG. 4B is a cross-sectional view illustrating an example test module with test leads.

DETAILED DESCRIPTION

Figure 1:
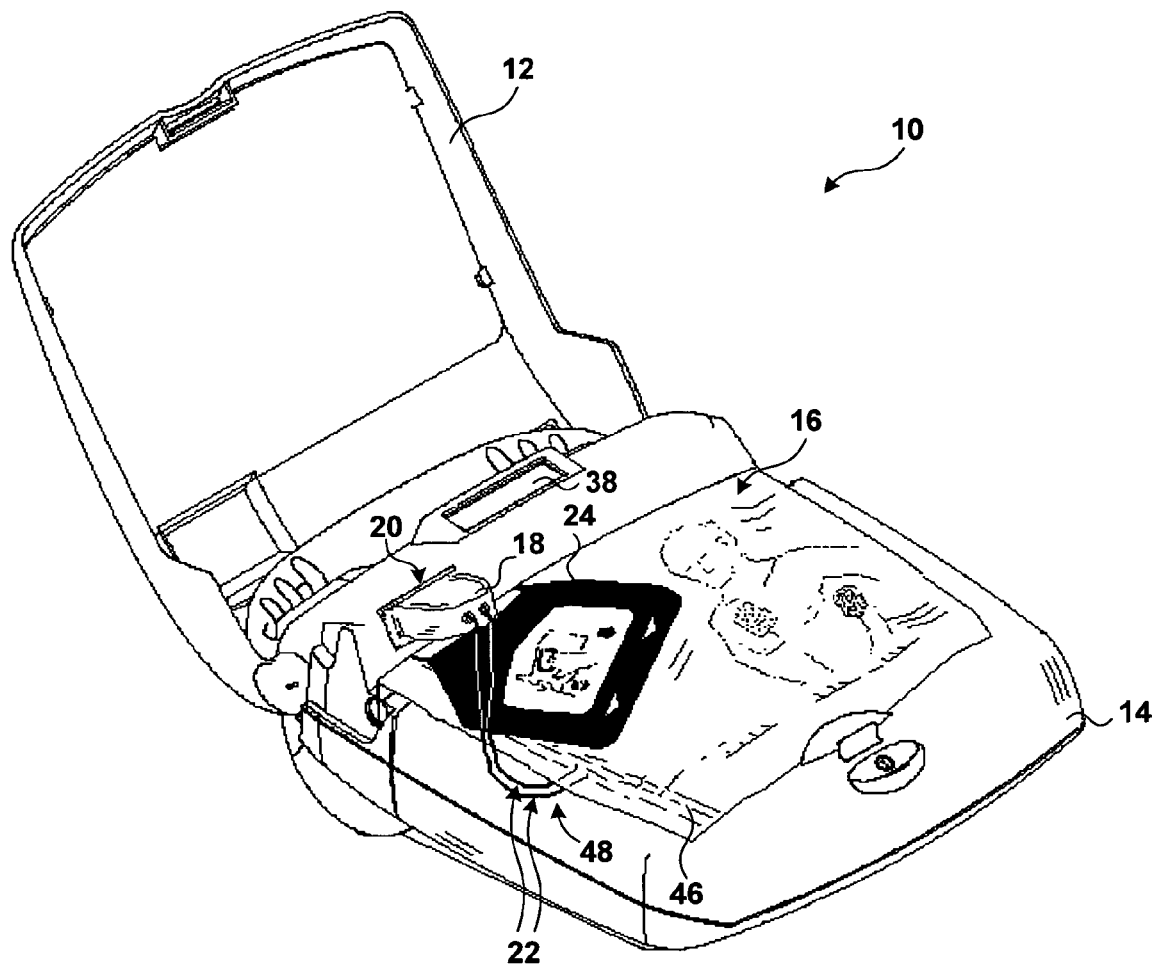
FIG. 1 is a perspective view of an example embodiment of an AED with a pouch that contains defibrillation electrodes.

FIG. 1 is a perspective view of an example embodiment of an AED 10, which is an example medical device that illustrates an embodiment of the invention. Although the invention will be described in the context of an AED and defibrillation electrodes that are coupled to the AED, but the invention is not limited to this application. Other medical devices monitor the patient or provide therapy to the patient, or both, and use medical electrodes to do so. Examples of such medical devices include, but are not limited to, patient monitors, fetal monitors, electrocardiograms, external cardiac pacemakers, electroencephalograms, and transneural stimulation units. In many cases, the medical electrodes used with these medical devices are stored in a sealed pouch, and many of them include hydrogel to enhances electrical contact between the electrode and the patient, and facilitate administration of therapy. It is often desirable that such medical electrodes be replaced when they are in a condition for replacement.

AED 10 includes cover 12, which is hingedly coupled to defibrillator case 14. Defibrillator case 14 includes circuitry (not shown in FIG. 1) that performs functions such as making measurements, processing cardiac signals, storing energy for delivery as a defibrillation pulse and regulating the delivery of the defibrillation pulse. Defibrillator case 14 also houses a power supply such as a battery (not shown in FIG. 1). In addition, defibrillator case 14 may include circuitry that controls automated voice instructions, other audible messages and readiness indicators and other visual indicators 38.

Pouch 16 rests atop defibrillator case 14. Pouch 16 is an example of a sealed package that can be used to implement the invention. Pouch 16 contains defibrillation electrodes 74 and 76 (not shown in FIG. 1). In case of an emergency, an operator removes electrodes 74 and 76 from pouch 16 and places electrodes 74 and 76 upon the chest of the patient.

Electrodes 74 and 76 are electrically coupled to defibrillator case 14 via insulated lead wires 22 and connector 18. Lead wires 22 extend from electrodes 74 and 76 through sealed entry point 48 in pouch 16, and are coupled to connector 18. Connector 18 mates to receptacle 20 in defibrillator case 14. When defibrillation electrodes 74 and 76 are applied to the chest of a patient, signals sensed via electrodes 74 and 76 are supplied to one or more processors in defibrillator case 14 via insulated lead wires 22 and connector 18. Similarly, defibrillation pulses are supplied from energy storage circuitry in defibrillator case 14 to electrodes 74 and 76 via connector 18 and insulated lead wires 22.

Pouch 16 can be removably fastened to defibrillator case 14 and is easily replaceable. As such, electrodes 74 and 76 and pouch 16 are not permanently coupled to defibrillation case 14. Rather, pouch 16 can be replaced by unfastening pouch 16 from defibrillator case 14 and uncoupling connector 18 from receptacle 20. Pouch 16 has a usable shelf life, and it is advantageous to replace pouch 16 when the shelf life expires. In addition, pouch 16 is generally replaced after pouch 16 has been opened.

Electrodes 74 and 76 are hermetically sealed inside pouch 16 to protect electrodes 74 and 76 from the environment. Electrodes 74 and 76 include a hydrogel layer that hydrates the patient's skin, forms an interface with the patient and enhances the capacity of electrodes 74 and 76 to sense electrocardiogram signals from the patient. In addition, the hydrogel promotes adhesion of electrodes 74 and 76 to the skin and reduces the risk of burns to the patient when a defibrillation pulse is applied. Pouch 16 may be, for example, an airtight foil bag that prevents the hydrogel from drying out and losing its desirable properties. Because pouch 16 is hermetically sealed, the operator must open pouch 16 to obtain access to electrodes 74 and 76.

In the embodiment depicted in FIG. 1, pouch 16 includes large handle 24 near upper left corner of pouch 16. Handle 24 may be composed of a brightly colored plastic, such as red plastic, so that handle 24 is especially prominent. Handle 24 may be a ring-type handle as shown in FIG. 1, making handle 24 easy to clutch and pull. The operator tears pouch 16 open by pulling handle 24. Pouch 16 tears beginning at a notch at a top of one side, and continues to tear along tear strip 46. Tear strip 46 prevents the tear from cutting across pouch 16, potentially damaging electrodes 74 and 76. In one implementation, tear strip 46 comprises tape with embedded fibers that guide the tear. When pouch 16 is open, the operator may extract electrodes 74 and 76, or electrodes 74 and 76 may slip out of pouch 16 as the operator pulls handle 24. The operator retrieves electrodes 74 and 76 and places electrodes 74 and 76 on the patient.

Figure 2:
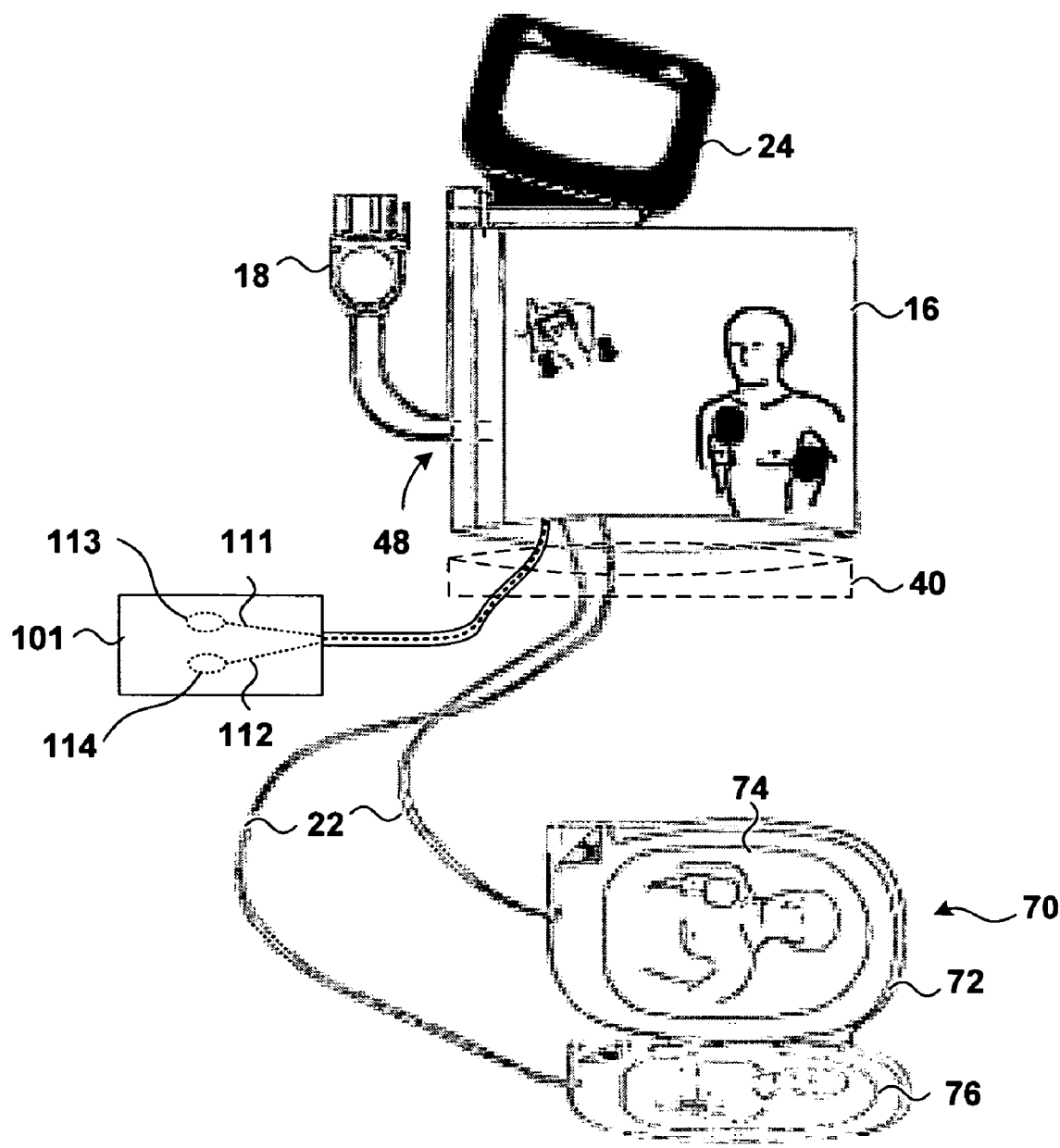
FIG. 2 is a view of an example embodiment of a pouch and an electrode assembly with a test module.

FIG. 2 is a view of pouch 16 and an electrode assembly 70 that is normally sealed inside pouch 16. Handle 24 has been flipped upward to show the obverse face of pouch 16. Electrode assembly 70 includes a right electrode 74 (also called an anterior electrode) and a left electrode 76 (also called a lateral electrode) affixed to a nonconductive plastic liner 72. Liner 72 is shown partially folded. When folded, liner 72 allows electrodes 74 and 76 to fit inside pouch 16. FIG. 2 further illustrates that a length of insulated lead wires 22 is coiled inside pouch 16. Bottom edge 40 of pouch 16 has been removed for purposes of illustration, and FIG. 2 is not intended to demonstrate how electrode assembly 70 is to be removed from pouch 16.

Electrodes 74 and 76 may each comprise a tin foil plate on a foam backing. The tin foil plates (not shown in FIG. 2) are electrically coupled to lead wires 22. The tin foil plates of electrodes 74 and 76, which in FIG. 2 are in contact with liner 72, are coated with a hydrogel that promotes adhesion of electrodes 74 and 76 to the skin of the patient. Electrodes 74 and 76 may also include additional adhesives to promote adhesion. Liner 72 prevents electrodes 74 and 76 from sticking to each other. The operator must remove liner 72 from electrodes 74 and 76 before applying electrodes 74 and 76 to the patient.

In the embodiment shown in FIG. 2, pouch 16 also contains a test module 101. Test module 101 includes a first test lead 111 and a second test lead 112. First test lead 111 and second test lead 112 may extend through sealed entry point 48 of pouch 16, and may be electrically coupled to connector 18. Accordingly, when connector 18 is coupled to a medical device such as an AED, defibrillation electrodes 74 and 76 and test module 101 are electrically coupled to the medical device.

Test module 101 is used to measure electrical operating characteristics of electrodes 74, 76. Over time, the electrical operating characteristics of electrodes 74, 76 change, due to exposure to various environmental conditions such as heat and humidity. In one embodiment, test module 101 is constructed in a manner similar to, or identical to, electrodes 74, 76. In other words, test module 101 can be constructed using the same materials as electrodes 74, 76, including liner and hydrogel. These materials may be obtained from the same batch and lot as the materials used to make electrodes 74, 76. Unlike electrodes 74 and 76, however, test module 101 is a "dummy," i.e., test module 101 includes many of the components used in defibrillation electrodes 74 and 76 but is not a functional defibrillation electrode. When test module 101 is placed inside sealed pouch 16 along with electrodes 74, 76, test module 101 is subjected to the same environmental conditions as electrodes 74, 76. Accordingly, the materials in test module 101, including the hydrogel, are subjected to the same environmental conditions as the functional defibrillation electrodes 74, 76 during their shelf life from manufacture, shipping and storage. As a result, the characteristics of test module 101 may reasonably be expected to reflect operational characteristics of electrodes 74, 76.

With this arrangement, AED 10 may periodically determine whether defibrillation electrodes 74 and 76 are in a condition for replacement by measuring characteristics of test module 101. In one embodiment, AED 10 may measure an impedance of test module 101 and may determine whether defibrillation electrodes 74 and 76 are in a condition for replacement as a function of the impedance measurement. In particular, AED 10 may energize a first terminal 113 on first test lead 111 and measure an impedance between first test lead 111 and second test lead 112, which are electrically coupled by hydrogel. AED 10 may, for example, supply a known test current to first terminal 113 and measure the voltage that develops as the test current flows from first terminal 113 through the hydrogel to a second terminal 114 on second test lead 112. The measured impedance is a function of the voltage divided by the current.

Measuring impedance is one way to determine the state of hydrogel included in test module 101, which is indicative of the condition of the hydrogel included in defibrillation electrodes 74, 76. Typically, impedance changes in the hydrogel occur because of environmental conditions under which electrodes 74, 76 are stored. Two of the most influential environmental conditions are temperature and humidity. In general, high temperature ages the defibrillation electrode, and low humidity tends to dry the hydrogel and degrade the desirable qualities of the hydrogel. High humidity, by contrast, tends to preserve those desirable qualities.

In an environment of high heat and low humidity, for example, the hydrogel tends to lose moisture and become less conductive, and as a result, the impedance of the hydrogel changes. Terminals 113 and 114 are electrically isolated from the foil plates of electrodes 74 and 76, but test module 101 is constructed from similar materials as defibrillation electrodes 74 and 76, and is stored in the same pouch 16 as defibrillation electrodes 74 and 76. Accordingly, measured changes in the impedance of the hydrogel in test module 101 will likely reflect changes in the impedance of the hydrogel on defibrillation electrodes 74 and 76 as well. When the measured impedance surpasses a predetermined value, either by going above or below a predetermined value, electrodes 74, 76 may be considered to be in a condition for replacement. For example, when the resistive portion of the impedance is deemed reflective of the condition of the hydrogel, electrodes 74, 76 may be in condition for replacement when the measured resistance exceeds a predetermined resistance, or when the measured conductance falls below a predetermined conductance.

Use of test module 101 may present one or more advantages. For example, it is possible to measure the impedance in test module 101 without subjecting defibrillation electrode to electrical excitation. In addition, test module 101 does not affect the use or operation of electrodes 74, 76.

Although test module 101 is depicted in FIG. 2 as being removed from the interior of pouch 16, test module 101 may be configured to remain inside pouch 16 when pouch 16 is opened. Test module 101 could therefore be unseen by the operator, and could be out of the operator's way. In an embodiment illustrated in FIG. 4C, the test module can be deployed on the same pad or backing that supports the defibrillation electrode. The invention is not limited to any particular deployment of test module 101, however.

Figure 3:
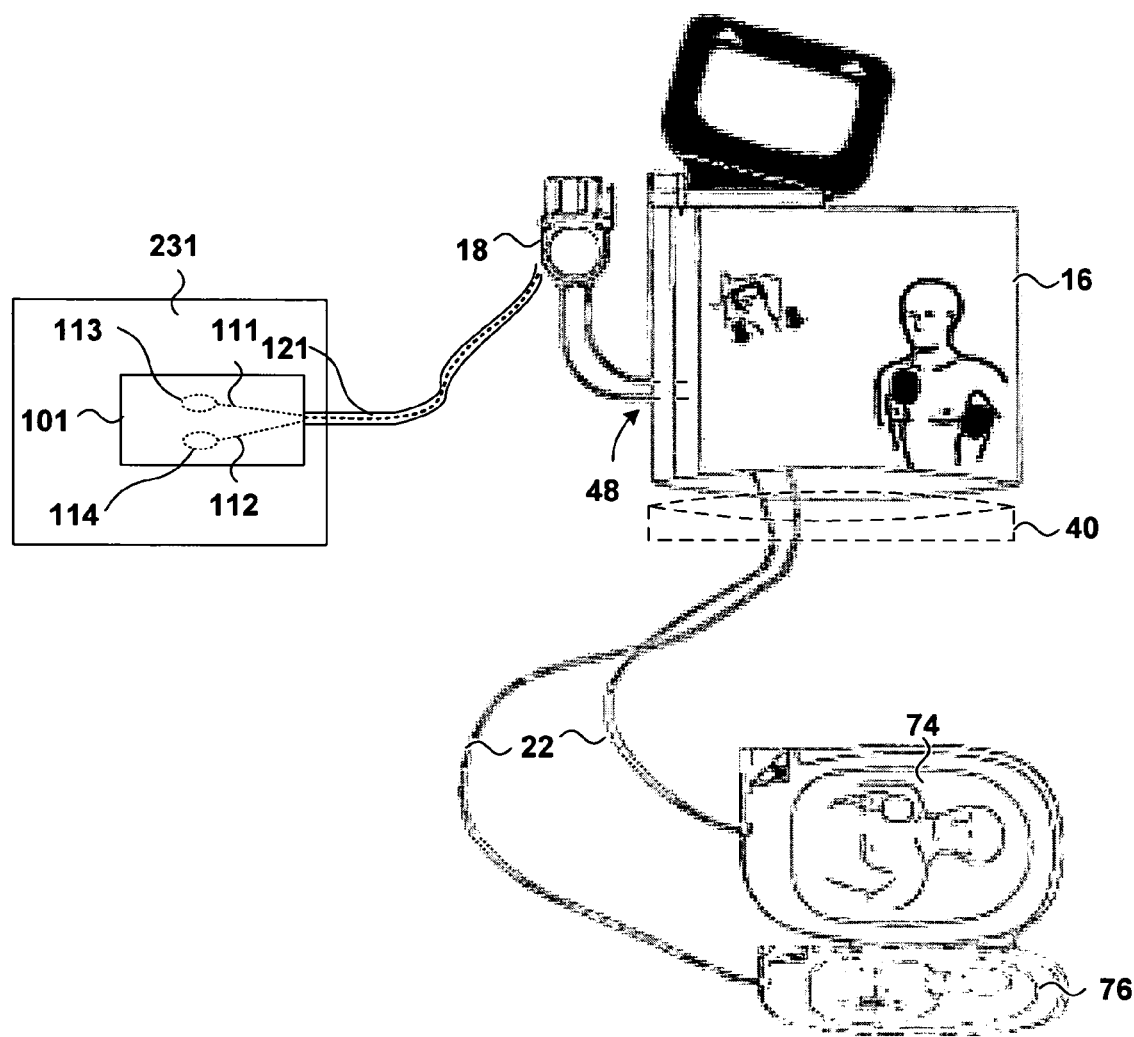
FIG. 3 is a view of another embodiment of a pouch and an electrode assembly and a test module.

FIG. 3 is a view of another embodiment of a pouch and an electrode assembly. The embodiment depicted in FIG. 3 is similar in many respects to the embodiment depicted in FIG. 2. In particular, pouch 16 contains electrodes 74, 76 and lead wires 22, and may be opened using handle 24.

In the embodiment depicted in FIG. 3, however, test module 101 is not deployed inside pouch 16. Rather, test module 101 is deployed within a separate hermetically sealed package such as test pouch 231. In this embodiment, test leads 121 may be coupled to connector 18 without passing through entry point 48 in pouch 16. An advantage of such an arrangement is that test module 101 may be deployed in a convenient location. In one configuration, test pouch 231 may be affixed back-to-back with pouch 16. In another configuration, test pouch 231 may be a sub-pouch of pouch 16.

Test pouch 231 may be constructed from similar materials and in a similar manner as pouch 16 and thus provide test module 101 with environmental conditions similar to environmental conditions experienced by electrodes 74, 76 within hermetically sealed pouch 16. When connector 18 is coupled to AED 10, AED 10 may measure an impedance between first terminal 113 on first test lead 111 and second terminal 114 on second test lead 112. AED 10 determines whether defibrillation electrodes 74, 76 are in a condition for replacement as a function of the impedance measurement.

Test module 101 shown in FIGS. 2 and 3 may be tested by AED 10 to determine when electrodes 74, 76 are in a condition for replacement. This testing may occur on a predetermined schedule or occur in response to a test command. Such a test command may be provided to AED 10 by a test button depressed by an operator or may be received from another device via a communications module. In one exemplary implementation, a central station may periodically interrogate AED 10 concerning the status of defibrillation electrodes 74, 76. In response, AED 10 measures the impedance between first test lead 111 and second test lead 112, determining whether defibrillation electrodes 74, 76 are in a condition for replacement as a function of the measurement, and transmits the determination to the central station via the communication module. In this implementation, AED 10 can notify the central station of a need to replace electrodes 74, 76. In another exemplary implementation, AED 10 measures the impedance and makes the determination when AED 10 is turned on as part of a self-test procedure. In a further exemplary implementation, AED 10 measures the impedance and makes the determination on a periodic basis. AED 10 may notify a person about the status of electrodes 74, 76 using visual display 38, using an audio output such as an alarm, transmitting a message to the central station, or using any other indication of status.

The invention is not limited to the embodiments depicted in FIGS. 2 and 3. For example, test module 101 need not be constructed using the same materials as electrodes 74, 76. For example, hydrogel used in test module 101 may be replaced with other electrically conductive materials, such as various salts that experience impedance changes when subjected to environmental conditions. The impedance of the substitute materials may reflect the impedance of the hydrogel on defibrillation electrodes 74, 76 even though the impedance for substitute materials need not be identical to impedance of the hydrogel used in electrodes 74, 76.

In addition to the above embodiments, test pouch 231 shown in FIG. 3 is illustrated as a separate pouch from pouch 16. In another embodiment, test pouch 231 may be a hermetically sealed pouch coupled to the interior or exterior of pouch 16. As mentioned above, test pouch 231 may be affixed to one side of pouch 16 in a back-to-back fashion to keep test pouch 231 unseen or otherwise out of the way of an operator. Test pouch 231 may be affixed to pouch 16 in other ways as well, or may be separate from pouch 16. The invention is not limited to any particular deployment of test pouch 231.

FIG. 4A is a cross-sectional view of a defibrillation electrode assembly 401 with built-in test leads 111 and 112, according to another embodiment of the invention. In the embodiment depicted in FIG. 4A, test leads 111 and 112 are deployed proximate to a working defibrillation electrode rather than a test module. In particular, defibrillation electrode assembly 401 includes an electrode plate 413 mounted on a non-conductive backing or pad 415. Although defibrillation electrode assembly 401 may be referred to conventionally as a "defibrillation electrode," plate 413 is the electrode component of defibrillation electrode assembly 401, i.e., plate 413 is the electrode component that conducts current from the defibrillation electrode assembly 401 to the patient.

Electrode plate 413 is coated with a hydrogel 411, which is in electrical contact with terminals 113 and 114. Hydrogel 411 between terminals 113 and 114 serves as an electrically conductive "bridge," such that current passing through terminals 113, 114 passes through at least a portion of hydrogel bridge 411. In addition, terminals 113, 114 are electrically isolated from electrode plate 413, such that such that current passing through terminals 113, 114 does not pass directly through plate 413. In this way, current flowing between terminals 113, 114 and the voltage between terminals 113, 114 can be used to determine an impedance of at least a portion of hydrogel bridge 411. A liner 414 covers hydrogel bridge 411, terminals 113 and 114, and electrode plate 413.

First test lead 111 and second test lead 112 need not be deployed exactly as depicted in FIG. 4A. Terminals 113 and 114 may be deployed flush with electrode plate 413, for example, or leads 111, 112 may be constructed as printed circuits upon a non-conductive layer of electrode 401. In one embodiment, terminals 113 and 114 may be deployed on opposing sides of electrode plate 413, which would support measurement of impedance of hydrogel 411 across the central portion of electrode plate 413. In another embodiment, terminals 113, 114 may be deployed in a location proximate to one side of electrode plate 413, and thus out of the way from the central portion of electrode plate 413. Many such arrangements for terminals 113, 114 may be used in accordance with principles of the invention, and the invention is not limited to any particular deployment of test leads or terminals.

In the embodiment shown in FIG. 4A, the AED measures an impedance between first test lead 111 and a second test lead 112, which is a function of the impedance of hydrogel bridge 411 between the leads. The AED determines whether defibrillation electrode 401 is in a condition for replacement as a function of the measurement. An advantage of a defibrillation electrode with built-in test leads is that the conductivity of the hydrogel used on the defibrillation electrode can be tested directly. In other words, an advantage of the configuration depicted in FIG. 4A is that the conductivity of the hydrogel actually deployed on a working defibrillation electrode can be tested.

FIG. 4B is a cross-sectional view of a test module assembly 417 according to another embodiment of the invention. Test module assembly 417 could be implemented, for example, in the embodiments of the invention shown in FIGS. 2 and 3. Test module assembly 417 is similar to defibrillation electrode assembly 401 shown in FIG. 4A, 401, having test leads 111 and 112 with terminals 113 and 114, hydrogel bridge 411, liner 414 and backing 415. Unlike defibrillation electrode assembly 401, test module assembly 417 does not include a working defibrillation electrode in contact with hydrogel bridge 411. Terminals 113, 114 may be deployed in contact with hydrogel bridge 411 in any fashion.

In the embodiment shown in FIG. 4B, the AED measures an impedance between first test lead 111 and a second test lead 112, which is a function of the impedance of the hydrogel bridge 411 between the leads. The AED determines whether a defibrillation electrode, typically subjected to the same environmental conditions as test module assembly 417 but not in electrical contact with test module assembly 417, is in a condition for replacement as a function of the measurement. Test module assembly 417 may be deployed in the same pouch that contains the defibrillation electrode or in a test pouch like test pouch 231 shown in FIG. 3.

Figure 4C:
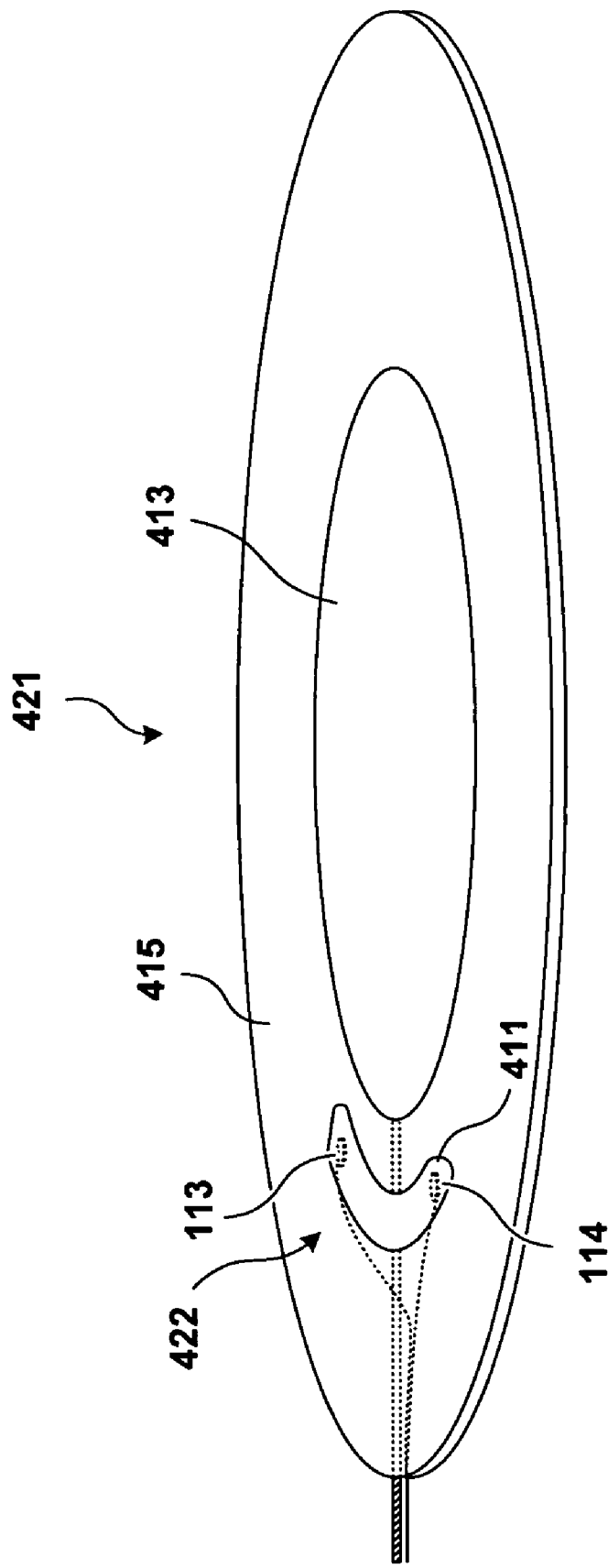
FIG. 4C is a perspective view illustrating an example embodiment of a defibrillation electrode with a test module.

FIG. 4C is a perspective view of a defibrillation electrode assembly 421 that includes a test module 422. In the embodiment depicted in FIG. 4C, terminals 113 and 114 are physically separated from and electrically isolated from working defibrillation electrode plate 413. In addition, the embodiment depicted in FIG. 4C includes a hydrogel bridge 411 that is in electrical contact with terminals 113 and 114 but is electrically isolated from plate 413 and from the hydrogel layer (not shown) on electrode plate 413. In this embodiment, defibrillation electrode plate 413 and test module 422 are coupled to backing 415. Accordingly, both electrode plate 413 and test module 422 are ordinarily covered by a single liner (not shown in FIG. 4C) and are stored in the same sealed pouch. As a result, test module 422 is subject to the same conditions as the working defibrillation electrode, so measurement of the impedance of gel bridge 411 can be a good indicator of the condition of the gel on electrode plate 413.

In the embodiment depicted in FIG. 4C, hydrogel bridge 411 has less surface area than the hydrogel covering electrode plate 413. As a result, in the event hydrogel on backing 415 starts to lose moisture, gel bridge 411 is likely to dry much more quickly than the gel on electrode plate 413, because of the smaller surface area of bridge 411. In other words, in the event environmental conditions are adversely affecting electrode 421, the environmental conditions will adversely affect test module 422 before the working defibrillation electrode, providing advance warning that the working defibrillation electrode is in condition for replacement.

FIG. 4C shows one of many implementations of a test module and a working electrode sharing a pad, and the invention is not limited to this particular configuration. For example, the invention supports an embodiment in which gel bridge 411 comprises a ring of hydrogel on backing 415 around, but electrically isolated from, defibrillation electrode plate 413. The invention also supports embodiments in which gel bridge 411 is an extension of the hydrogel on plate 413, or is otherwise in electrical contact with the hydrogel on defibrillation electrode plate 413. The invention further supports an embodiment in which electrode plate 413 is mounted to backing 415, but test leads 111 and 112 and terminals 113 and 114 are coupled to the liner rather than to backing 415. In this embodiment, the liner covers electrode plate 413 and test module 422, but leads 111 and 112 and terminals 113 and 114 are peeled away from backing 415 when the operator removes the liner.

Figure 5:
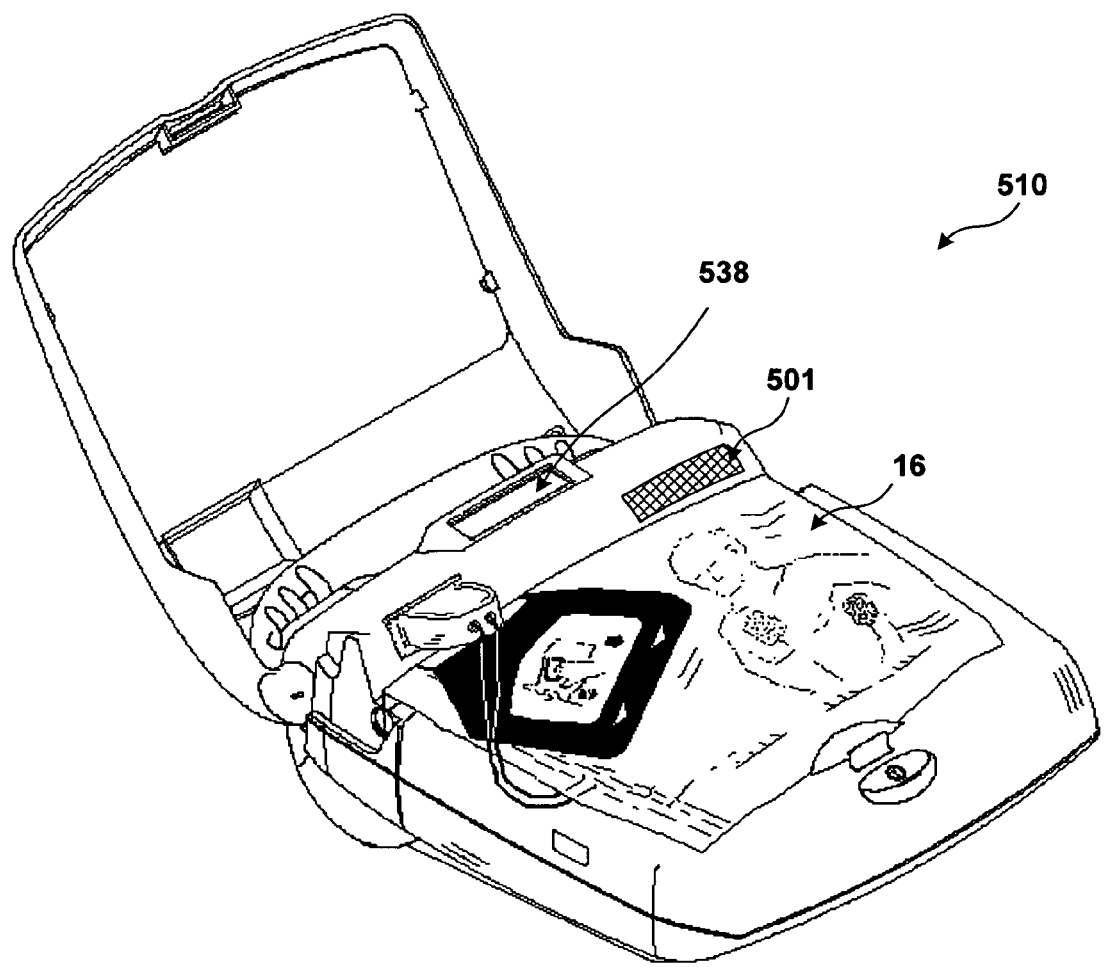
FIG. 5 is a perspective view of an another embodiment of an AED including one or more environmental sensors.

FIG. 5 is a perspective view of another embodiment of an AED 510. AED 510 is like AED 10 shown in FIG. 1, except AED 510 includes one or more environmental sensors 501. AED 510 collects data about environmental conditions, such as temperature and humidity data, via environmental sensors 501, and determines whether defibrillation electrodes stored in pouch 16 are in a condition for replacement as a function of the environmental condition data. Although shown deployed on the surface of AED 510, environmental sensors 501 may be deployed elsewhere. For example, environmental sensors 501 may be deployed inside pouch 16 or inside a test pouch like test pouch 231 shown in FIG. 3.

Environmental sensors 501 may comprise, for example, a temperature sensor and a humidity sensor. The temperature sensor may include one or more sensors that respond to temperature, such as a thermocouple. Similarly, the humidity sensor data may include one or more sensors that respond to humidity, such as an electronic psychrometer. The invention supports any kind of environmental sensors and is not limited to any particular environmental sensor.

AED 510 periodically obtains environmental condition data from environmental sensors 601 and stores the environmental condition data in memory in AED 510. In one embodiment, environmental sensors 501 measure temperature and humidity environmental condition data. AED 510 estimates useful shelf life for electrodes 74, 76 (not shown in FIG. 5) by comparing this temperature and humidity environmental condition data with previously loaded temperature and humidity shelf life curves. The temperature and humidity shelf life curves may be empirically based. That is, the relationships between shelf life and one or more environmental conditions may be discovered by experimentation.

For example, the temperature and humidity environmental condition data obtained from environmental sensors 501 may be averaged to obtain an average temperature and humidity values. These averaged data may be compared to shelf life estimates that are based upon experimental testing. AED 510 may, for instance, find the observed average temperature and average humidity values in a look-up table, and determine the shelf life associated with the observed values. In this way, a useful shelf life for electrodes 74, 76 may be measured as a function of the actual average temperature and average humidity to which electrodes 74, 76 are subjected. The invention is not limited to average temperature and average humidity values, but supports other measurements of environmental conditions as well.

When a new pouch 16 containing electrodes 74, 76 is coupled to AED 510, AED 510 resets ongoing average temperature and humidity values being maintained for estimating shelf life. If a date of manufacture or an expiration date for pouch 16 is entered into AED 510, AED 510 may determine the shelf life as a function of this date and as a function of observed average temperature and humidity values. In other words, AED 10 may use a manufacturer's manufacture or an expiration date as a starting point for determining the usable shelf life, and may adjust the determination as a function of environmental factors.

The date of manufacture or expiration date for pouch 16 may be entered by an operator at the time of installation of pouch 16. Alternatively, a date of manufacture or expiration date for pouch 16 may be encoded and written on pouch 16. At time of installation of pouch 16, AED 510 may automatically read the date for use in determining an expiration date for pouch 16.

For example, a date of manufacture data may be written onto pouch 16 in computer readable characters or in bar code form. AED 510 may contain a corresponding reader to retrieve this date of manufacture. This data reader may be an integral part of AED 510 or may be an removable device that may be connected to AED 510 by an operator when pouch 16 is installed. In another example, the date of manufacture may be written on a magnetic media strip that is a part of pouch 16 and is read by a magnetic reader. In a further example, an operator may enter the date of manufacture by hand. The invention supports these and any other methods of data encoding and entry.

If AED 510 includes a clock to indicate a present date, expiration of an estimated shelf life may be used to trigger alarm indicators that electrodes 74, 76 within pouch 16 needs replacing. For example, AED 510 may indicate an alarm when one year after the manufacturing date has elapsed. The elapsed time may be lengthened or shortened depending upon environmental conditions. When the data obtained from environmental sensors 501 indicate that average temperatures have been normal and that average humidity values have been above normal, for instance, AED 510 may indicate an alarm when more than one year after the manufacturing date has elapsed. When the data obtained from environmental sensors 501 indicate that average temperatures have been high and that average humidity values have been below normal, by contrast, AED 510 may indicate an alarm when less than one year after the manufacturing date has elapsed.

The alarm indicators may output data upon display device 538. The alarm indicators may also output other visual and auditory alarm indications such as activating an error light and generating an error beep that may be observed by an operator.

While temperature and humidity environmental condition data is described herein, any other combination of environmental conditions measurable by AED 510 may be used, alone or in combination, to estimate shelf life for electrodes 74, 76 as long as experimental test data provides a reasonable correlation between estimated shelf life and observed environmental condition data. In addition, the above embodiment describes using an average value for temperature and humidity. These data averages may correspond to an average values calculated over the entire life of the electrodes or may represent and average value for a fixed period of time or a fixed number of observed data values. Furthermore, the invention is not limited to use of averages. AED 510 may estimate a shelf life for a defibrillation electrode as a function of the peak temperature or humidity values, for example.

The above embodiments for environmental sensors 501 provide electronic data corresponding to environmental conditions affecting shelf life of electrodes 74, 76 and whether electrodes 74, 76 are in a condition for replacement. The invention also supports the use of non-electronic sensors for measurement of environmental conditions affecting shelf life. For example, chemically based solutions may be placed upon an indicator that dries out when exposed to extended periods of heat and humidity. As the solution dries, the indicator may change its color. Experimental data may correlate the change in color for the chemically based indicator with electrode shelf life. In this way, a useful shelf life indicator may be constructed.

Figure 6:
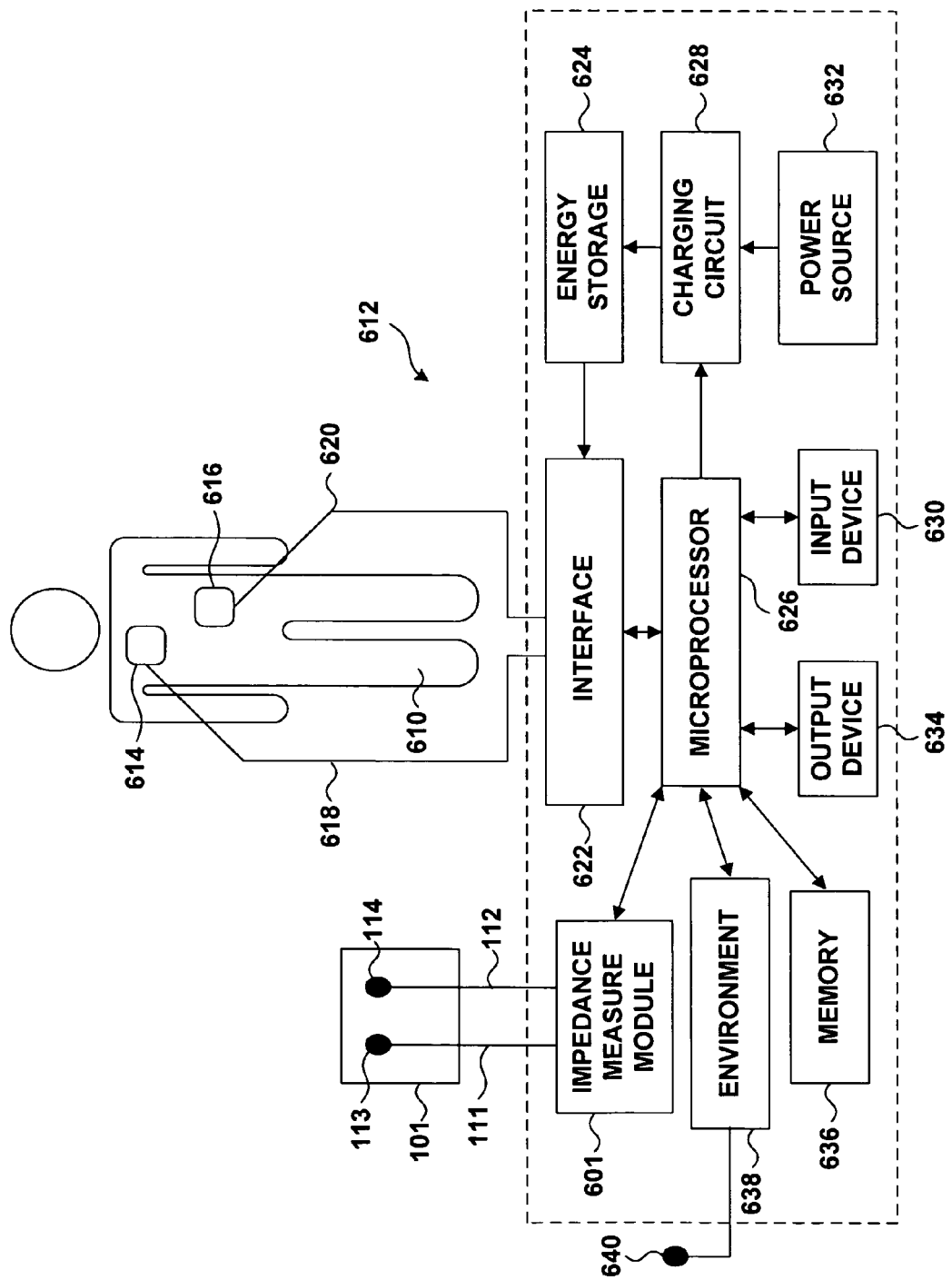
FIG. 6 is a block diagram of a processing system within an AED.

FIG. 6 is a block diagram showing a patient 10 coupled to an external defibrillator 612. External defibrillator 612 is one example of a medical device that may be used to practice the invention. Defibrillator 612 may be, for example, an AED, but the techniques of the invention may be practiced with a manual defibrillator and other medical devices as well.

Defibrillator 612 is capable of administering defibrillation therapy to patient 610 via electrodes 614 and 616, which may be adhesive electrode pads placed externally on the skin of patient 610. As shown in FIG. 6, defibrillation electrodes 614, 616 have been removed from a hermitically sealed pouch and have been deployed on the body of patient 610. The body of patient 610 provides an electrical path between electrodes 614 and 616.

Electrodes 614 and 616 are coupled to defibrillator 612 via conductors 618 and 620 and interface 622. In a typical application, interface 622 includes a receptacle, and connectors 618, 620 plug into the receptacle. Electrical impulses or signals may be sensed by defibrillator 612 via electrodes 614 and 616 and interface 622. Electrical impulses or signals may also be delivered from defibrillator 612 to patient 610 via electrodes 614 and 616 and interface 622.

Energy storage device 624 stores energy for fibrillation and defibrillation therapy in energy storage components, such one or more charged capacitors. Interface 622 includes one or more switches (not shown in FIG. 6) that, when activated, deliver energy stored in an energy storage device 624 to electrodes 614 and 616. Energy storage device 624 and interface 622 cooperate to function as an electrical source that generates therapeutic electrical shocks that deliver the therapy to patient 610. Interface 622, in addition to controlling when current may flow to patient 610, may also regulate the direction of current flow, under the control of a microprocessor 626.

Microprocessor 626 may evaluate the electrical activity in the heart of patient 610 sensed via electrodes 614 and 616. Microprocessor 626 may, for example, apply algorithms to determine whether patient 610 exhibits a normal heart rhythm or an arrhythmia. Microprocessor 626 may further estimate the likely effectiveness of therapy for an arrhythmia.

Before energy may be delivered to patient 610 as part of defibrillation therapy, charging circuit 628 stores energy in energy storage device 624. Microprocessor 626 directs charging circuit 628 to charge energy storage device 624 to a high voltage level. Charging circuit 628 comprises, for example, a flyback charger that transfers energy from a power source 632 such as a battery to energy storage device 624. Charging circuit 628 transfers energy from power source 632 to energy storage device 624 until the energy stored in energy storage device 624 reaches a desired level. At that point, defibrillator 612 is ready to deliver a therapeutic shock. The therapy may be delivered automatically or manually.

The effectiveness of the therapy is a function of the conductivity between the body of patient 610 and defibrillation electrodes 614 and 616. The conductivity between the body of patient 610 and defibrillation electrodes 614 and 616 is a function of the quality of the hydrogel applied to defibrillation electrodes 614 and 616. If defibrillation electrodes 614 and 616 are in a condition for replacement, there is an increased risk that the hydrogel on electrodes 614 and 616 will provide poor conduction.

Accordingly, microprocessor 626 determines whether defibrillation electrodes 614 and 616 are in a condition for replacement. Microprocessor 626 controls impedance measure module 601 to measure impedance between terminals 113 and 114. Impedance measure module 601 may, for example, include a current source that generates a known current flowing between terminals 113 and 114, and a detector that measures the voltage developed between terminals 113 and 114. Microprocessor 626 computes the impedance as a function of the current and voltage, and determines the state of the hydrogel as a function of the impedance. Microprocessor 626 may generate alarm signals via one or more output devices 634 when impedance measurements are outside an acceptable range.

Defibrillator 612 may receive information pertaining to the shelf life, such as a date of manufacture or an expiration date, via one or more input devices 630. In addition, defibrillator may include an environmental module 638 that receives environmental data from one or more environmental sensors 640. Data such as date of manufacture and environmental data may be stored in memory 636. Temperature and humidity shelf life curves, as described above, may also be stored in memory 636. Memory 636 also stores instructions that direct the operation of microprocessor 626, and further stores information about patient 610 and defibrillator 612.

Test module 101, which includes terminals 113 and 114, and environmental sensors 640 may be deployed in any of several ways. Test module 101 and environmental sensors 640 may be deployed inside the hermitically sealed pouch that contained defibrillation electrodes 614, 616, for example, or inside a test pouch.

Defibrillator 612 may receive an interrogation that prompts microprocessor 626 to determine whether defibrillation electrodes 614, 616 have exceeded a usable shelf life or otherwise are in a condition for replacement. The interrogation may be received from a user request via an input device 630, or from a remote device, such as a central station, via a communication module (not shown). In response to the interrogation, microprocessor 626 determines whether defibrillation electrodes 614, 616 are in a condition for replacement and responds to the interrogation. Microprocessor 626 may, for example, output an alarm signal or an "OK" signal via output device 634, or may transmit the determination to the remote device via the communication module.

Figure 7:
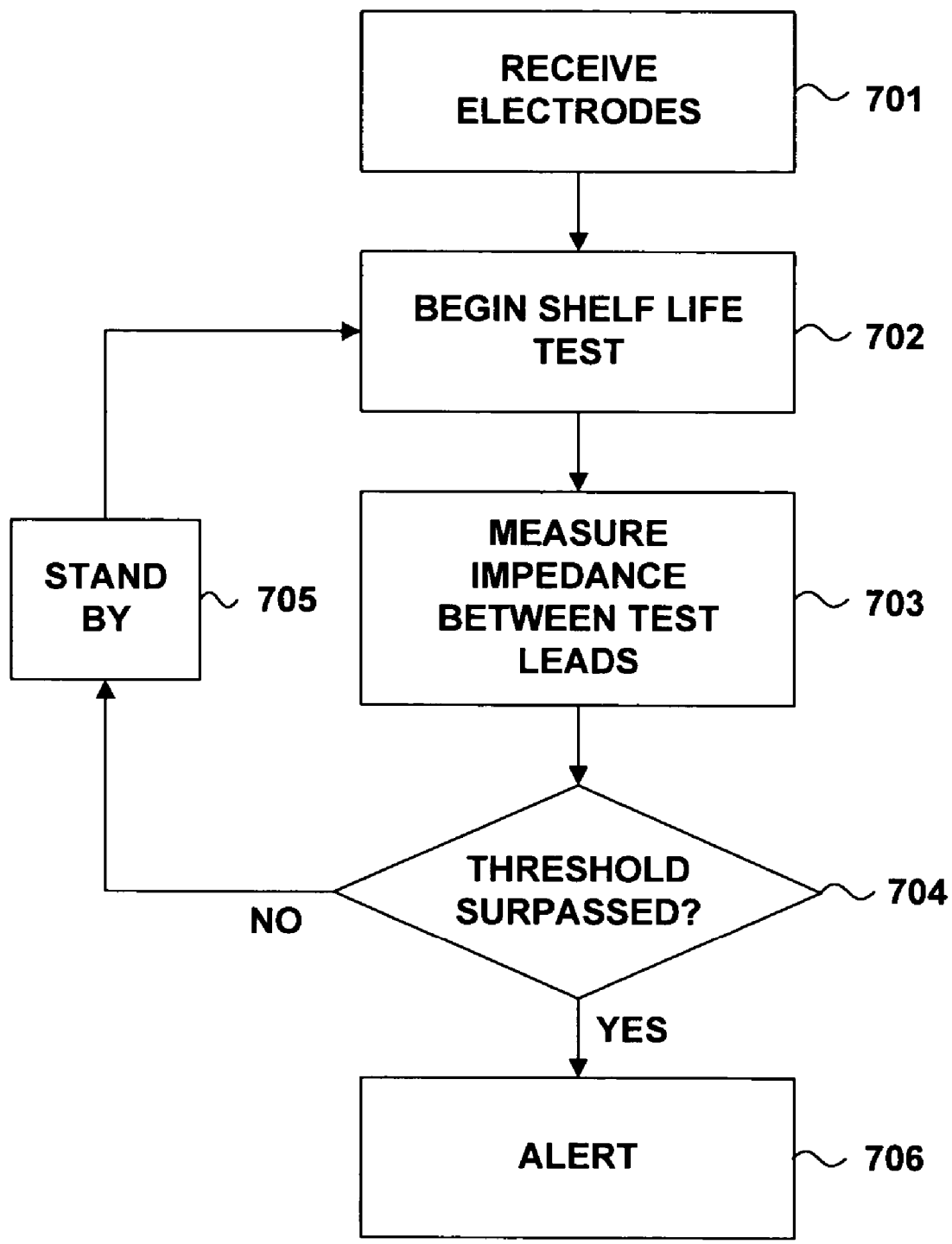
FIG. 7 is a flow diagram illustrating an example mode of operation according to an embodiment of the invention.

FIG. 7 is a flow diagram illustrating an example mode of operation of a medical device such as AED 10, AED 510 or defibrillator 612. A determination of estimated shelf life for a particular set of electrodes may begin when the medical electrodes are coupled to the medical device (701). At this time, the medical device may receive a date of manufacture or an expiration date, which may be of use in determining whether shelf life for the medical electrodes has expired.

The medical device tests the condition of the medical electrodes (702). As discussed above, such a test may include measurements of impedance of a hydrogel. A measuring element such as impedance measure module 601 measure impedance between test leads (703). The measured impedance is indicative of the condition of operating conditions the medical electrodes.

The medical device compares the measured impedance with a predetermined threshold value (704) to determine whether the medical electrodes are in a condition for replacement. When the observed impedance is found to be greater than a predetermined threshold value, for example, or when the observed admittance is below a predetermined threshold value, the medical device may generate an alert (706) to indicate that the medical electrodes are in a condition for replacement. The alert may be presented locally, such as by an audible or visual alarm, or may be transmitted to a remote receiver such as a central station. When an alert is unwarranted, the medical device stands by (705) and may repeat the above-described impedance test on a periodic basis or upon command from a user or another device.

In some embodiments of the invention, the medical device tests the medical electrodes (702) in response to an interrogation by a user, and responds to the interrogation. In addition to determining whether the medical electrodes are in a condition for replacement, the medical device may supply other information as well. The medical device may, for example, display an updated expiration date.

Figure 8:
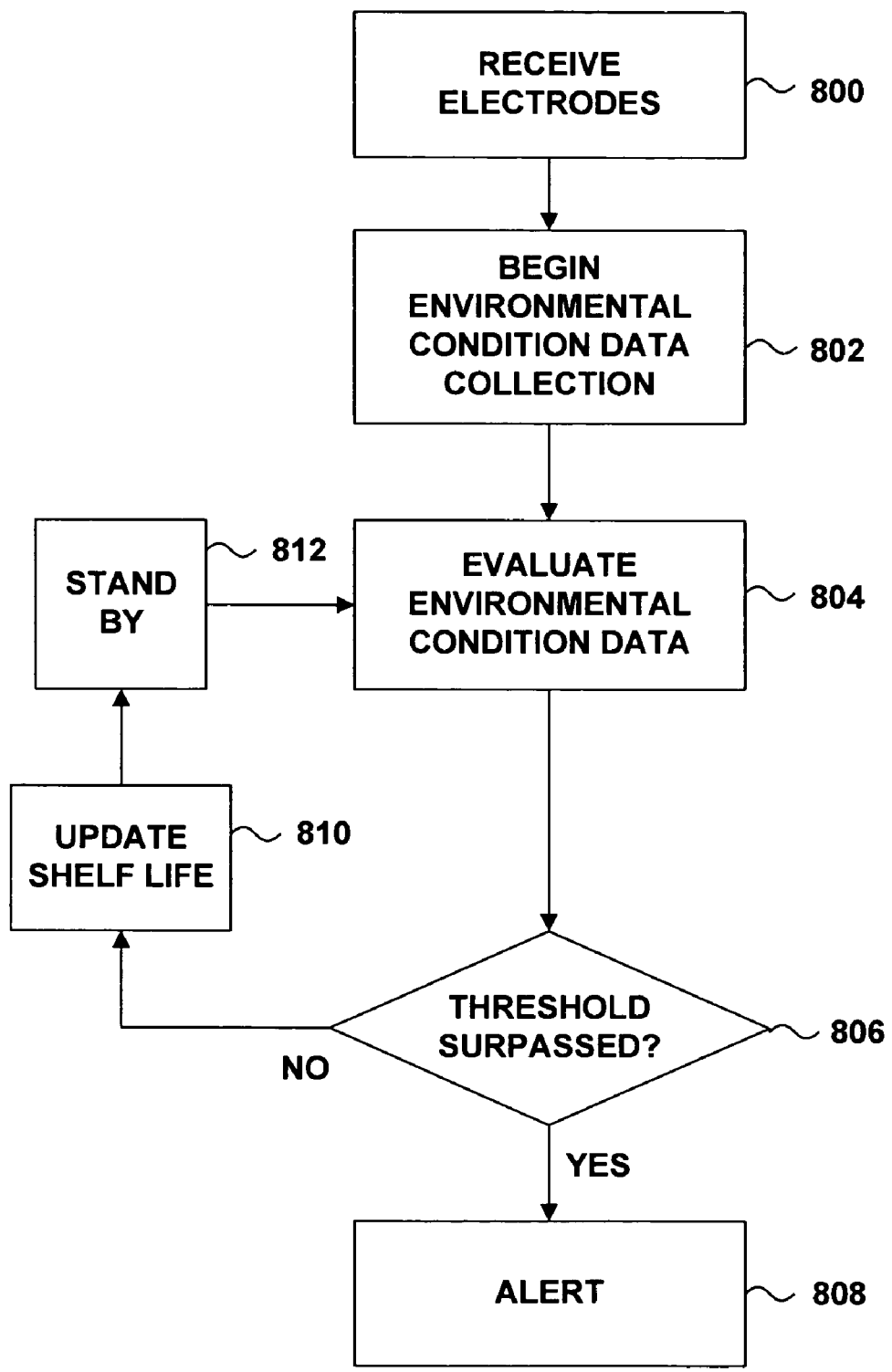
FIG. 8 is a flow diagram illustrating an example mode of operation according to another embodiment of the invention.

FIG. 8 is a flow diagram illustrating an example mode of operation of a medical device such as AED 510 or defibrillator 612. A determination of estimated shelf life for a particular set of medical electrodes may begin when the medical electrodes are coupled to the medical device (800). At this time, the medical device may receive a date of manufacture or an expiration date, which may be of use in determining whether shelf life for the medical electrodes has expired. The medical device may also reset environmental condition data, such as temperature and humidity data, stored in memory. Over time, the medical device receives or collects environmental condition data (802) via one or more environmental sensors.

The medical device evaluates or processes the environmental condition data (804), which is indicative of the condition of operating conditions the medical electrodes. The evaluation may include averaging of temperature and humidity data collected over time. The medical device compares the evaluated environmental condition data with a predetermined threshold (806) to determine whether the shelf life of the medical electrodes has expired. When the shelf life of the medical electrodes has expired, the medical device may generate an alert (808).

In some embodiments of the invention, when the shelf life of the medical electrodes has not expired, the medical device updates the expected shelf life of the medical electrodes (810). The medical device may estimate a shelf life anew, or adjust a pre-determined shelf life up or down as a function of the environmental condition data. The medical device may compare temperature and humidity environmental condition data with temperature and humidity shelf life curves, for example, and may update the expected usable shelf life as a function of the comparison. "Updating the shelf life" includes, but is not limited to, determining a new expected expiration date. The medical device may report the updated shelf life by way of an output device or a communication module. Other embodiments of the invention omit updating the expected shelf life (810). The medical device stands by (812), and may re-evaluate the environmental condition data (804) on a periodic basis or upon command or interrogation from a user or another device.

Like the techniques of FIG. 7, the techniques shown in FIG. 8 support embodiments in which the medical device evaluates conditions (804) in response to an interrogation. In addition to determining whether the medical electrodes are in a condition for replacement, the medical device may, for example, display an updated expiration date. When the environmental condition data suggests that the medical electrodes are deployed in a venue having moderate temperatures and high humidity, for example, the medical device may determine that the estimated expiration date has been moved further into the future.

The techniques shown in FIGS. 7 and 8 are not exclusive of one another. In various embodiments of the invention, a medical device determines whether medical electrodes are in a condition for replacement as a function of impedance and as a function of environmental condition data.

The invention may result in one or more advantages. A medical device that implements the invention may have an added degree of safety and reliability. Medical devices such as AEDs may sit idle for long periods of time. During a long idle period, medical electrodes such as defibrillation electrodes may silently lose effectiveness. When called into use, the medical electrodes may not be as effective as desired. The invention supports monitoring of the medical electrodes, and notifying a person when the medical electrodes are in a condition for replacement. As a result, the medical device is more likely to be equipped with medical electrodes that will operate well in an emergency.

Further, the invention supports an efficient use of medical electrodes such as defibrillation electrodes. In practice, not all medical electrodes have the same shelf life because not all medical electrodes lose functionality at the same rate. For example, some medical electrodes subjected to moderate temperatures and high humidity may have a considerably longer shelf life than medical electrodes subjected to high temperatures and low humidity. The invention therefore supports retaining medical electrodes that are still in good shape.

Various embodiments of the invention have been described. Various modifications may be made without departing from the scope of the claims. For example, a medical device can measure an impedance between test leads by measuring an admittance, or by measuring only a resistive component or reactive component of the impedance. Furthermore, the invention encompasses embodiments in which the medical electrodes are in a condition for replacement but are still usable. In other words, the invention is not limited to applications in which the medical electrodes are determined to be totally unusable.

Some of the techniques of the invention may be embodied as a computer-readable medium comprising instructions that cause a programmable processor, such as microprocessor 626 in FIG. 6, to carry out the techniques of the invention. The programmable processor may include one or more individual processors, which may act independently or in concert. A "computer-readable medium" includes but is not limited to read-only memory, Flash memory and a magnetic or optical storage medium. These and other embodiments are within the scope of the following claims.

The invention claimed is:

1. A method for determining a condition of a medical electrode which includes at least one plate capable of delivering electrical therapy when coupled to a medical device, comprising:
   measuring an impedance between a first test lead and a second test lead in electrical contact with a hydrogel bridge, each of the first test lead and the second test lead being electrically isolated from each of the at least one plates of the medical electrode; and
   determining whether the medical electrode is in a condition for replacement as a function of the measurement.

2. The method of claim 1, wherein the measuring an impedance comprises:
   supplying the first test lead with a test electrical current; and
   measuring the voltage between the first test lead and the second test lead as the test current flows from the first test lead to the second test lead through the hydrogel bridge.

3. The method of claim 1, further comprising:
   comparing the measurement to a threshold; and
   generating an alarm when the measurement surpasses the threshold.

4. The method of claim 1, further comprising:
   receiving at least one environmental condition datum from an environmental sensor; and
   determining the medical electrode to be in a condition for replacement as a function of the datum.

5. The method of claim 4, wherein the environmental condition datum comprises at least one of a temperature datum and a humidity datum.

6. The method of claim 1, further comprising updating a usable shelf life of the medical electrode as a function of the measurement.

7. The method of claim 1, wherein the medical electrode comprises a defibrillation electrode.

8. The method of claim 1, wherein the medical device comprises an automated external defibrillator.

9. A computer-readable medium comprising instructions to cause a programmable processor to determine whether a medical electrode which includes at least one plate capable of delivering electrical therapy coupled to a medical device is in a condition for replacement as a function of a measurement of an impedance between a first test lead and a second test lead in electrical contact with a hydrogel bridge, each of the first test lead and the second test lead electrically isolated from each of the at least one plates of the medical electrode which is coupled to a medical device for delivery of electrical therapy thererthrough.

10. The medium of claim 9, the instructions further causing the processor to generate an alarm when the processor determines that the medical electrode is in a condition for replacement.

11. The medium of claim 9, the instructions further causing the processor to determine whether the medical electrode is in a condition for replacement as a function of at least one environmental condition datum from an environmental sensor.

12. A device comprising:
   a first test lead;
   a second test lead;
   a hydrogel bridge in electrical contact with the first and second test leads, the first test lead and the second test lead electrically isolated from a therapy delivery plate of a medical electrode through which electrical therapy is deliverable when coupled to a medical device, wherein the therapy delivery plate includes all of the one or more plates of the medical electrode through which electrical therapy is deliverable when coupled to a medical device; and
   a hermetically sealed package containing the first and second test leads and the hydrogel bridge.

13. The device of claim 12, further comprising a connector configured to be coupled to the medical device.

14. The device of claim 12, wherein the hermetically sealed package contains the medical electrode.

15. The device of claim 12, further comprising an environmental sensor.

16. The device of claim 12, further comprising the therapy delivery plate of the medical electrode.

17. The device of claim 16, further comprising a non-conductive backing, wherein the therapy delivery plate, the first test lead and the second test lead are coupled to the backing.

18. The device of claim 17, further comprising a non-conductive liner configured to cover the first test lead, the second test lead, the hydrogel bridge and the therapy delivery plate of the medical electrode.

19. The device of claim 16, further comprising:
   a non-conductive backing; and
   a non-conductive liner; wherein the therapy delivery plate is coupled to the backing and the first test lead and the second test lead are coupled to the liner.

20. The device of claim 12, wherein the medical electrode comprises a defibrillation electrode.

21. The device of claim 12, wherein the medical device comprises an automated external defibrillator.

22. A device comprising:
   a first test lead;
   a second test lead;
   a plate of a medical electrode coupled to a medical device;
   a hydrogel bridge in electrical contact with the first and second test leads, the first test lead and the second test lead electrically isolated from the plate of the medical electrode;
   a hermetically sealed package containing the first and second test leads and the hydrogel bridge; and
   a hydrogel layer electrically isolated from the hydrogel bridge, the hydrogel layer in electrical contact with the plate of the medical electrode.

23. The device of claim 22, wherein the hydrogel bridge comprises a ring around the hydrogel layer.

* * * * *